United States Patent [19]

Thomas et al.

[11] 4,235,842
[45] Nov. 25, 1980

[54] TEMPERATURE CYCLE INDICATING MEANS FOR A STERILIZER UNIT

[75] Inventors: Michael D. Thomas, Arab, Ala.; Francis E. Ryder, Barrington, Ill.

[73] Assignee: Ryder International Corporation, Arab, Ala.

[21] Appl. No.: 955,392

[22] Filed: Oct. 27, 1978

[51] Int. Cl.³ .............................. A61L 2/04; H05B 1/00
[52] U.S. Cl. .................................. 422/116; 73/343 B; 73/343.5; 116/221; 116/284; 219/487; 219/510; 422/307
[58] Field of Search ................. 422/28, 109, 116, 300, 422/302, 307; 219/248, 269, 487, 506, 510; 73/343 R, 343 B, 343.5, 363.5, 76; 116/102, 216, 221, 284

[56] References Cited

U.S. PATENT DOCUMENTS

| | | | |
|---|---|---|---|
| 2,750,916 | 6/1956 | Hanington | 116/102 |
| 3,801,278 | 4/1974 | Wagner et al. | 422/307 X |
| 3,983,362 | 9/1976 | Hoogesteger et al. | 422/300 X |
| 4,158,126 | 6/1979 | Seitz | 422/307 X |

FOREIGN PATENT DOCUMENTS 1470141  4/1977  United Kingdom ................... 73/343 B

*Primary Examiner*—Arnold Turk

*Attorney, Agent, or Firm*—Trexler, Wolters, Bushnell & Fosse, Ltd.

[57] ABSTRACT

Contact lens disinfector unit for sterilizing contact lenses contained within a lens case, wherein the contact lenses are of the type which preferably should be sterilized or disinfected once each day and periodically cleaned after a predetermined number of sterilizing or disinfecting cycles. The heating unit includes a housing in which is disposed a heating block arranged to contact the lens case, and circuit means operatively associated with the heating block and adapted to be coupled to a source of electric potential for utilizing electric current to apply heat to the heating block. The circuit applies the electric current for a sufficient period of time to attain a desired sterilizing temperature within the case, and then terminates the heating cycle allowing the lens case and the contact lenses to cool, thereby completing the overall sterilizing cycle. The disinfector unit includes a cycle indicating arrangement which is responsive to the temperature changes of the heating block for providing a first indication upon reaching the sterilizing temperature and a second indication responsive to the heating block returning to a reduced temperature below the sterilizing temperature. The first indication indicates that the heating block is at an elevated temperature and the second indication indicates the number of sterilizing cycles which have been employed since the contact lenses were last cleaned.

19 Claims, 11 Drawing Figures

TEMPERATURE CYCLE INDICATING MEANS FOR A STERILIZER UNIT

BACKGROUND OF THE INVENTION

The present invention is directed generally to a contact lens disinfector unit, and more particularly to a disinfector unit including means providing an indication as to attainment of the sterilizing temperature, as well as the number of sterilizing cycles that have been employed since the last incident of cleaning of the lenses.

Contact lenses, both of the hard and soft type, often must be sterilized before they are suitable for use. To this end, each pair of contact lenses is inserted into a separate container or lens case which may also have receptacles therein for holding the right and left lenses spaced apart so they do not become confused. These containers are also commonly referred to as contact lens holders. A quantity of fluid is then administered to the container and then the container is placed into a disinfector unit having a heating block for heating the fluid to a sterilization temperature. The lens case is in direct contact with the heating block and the fluid within the container is in direct contact with the lenses and effects sterilization thereof. After the sterilization temperature has been reached and maintained for a sufficient period of time to effect sterilization of the lenses, the lens case and the contact lenses contained therein are permitted to cool to facilitate removal from the disinfector unit.

While both hard and soft contact lenses should be sterilized periodically, sterilization is more critical with respect to soft contact lenses, and daily sterilization is recommended. The reason for this is that soft contact lenses are hydrophilic, that is somewhat porous and therefor capable of absorption of liquid, which maintains the lenses in a soft condition. The porous nature of the lens material also provides a medium for bacterial growth, and as such soft lenses must be sterilized periodically to prevent infection. As an additional matter, the porous lens material will also absorb proteinaceous material which tends to solidify after repeated sterilizing operations, and as such can affect the lenses' corrective and viewing properties. Lens manufacturers therefore suggested and strongly recommended that the user employ a cleaning solution containing certain enzymes which attack and remove the proteinaceous material, after a prescribed number of sterilizing or disinfecting cycles, as for example once each week.

Heretofore, prior contact lens disinfector units, while generally successful, have not provided the user with heating cycle indicating means of the type contemplated by the present invention. More specifically, the invention illustrated and to be discussed provides an indication that the disinfector unit has reached the sterilization temperature, and also when the unit has cooled. Further, said indicator also indicates the number of sterilizing cycles completed since the last cleaning procedure for the proteinaceous material.

As mentioned above, soft contact lenses should be cleaned every predetermined number of days, such as once a week, for example. Prior disinfector units, however, have not provided a means by which the user may easily determine the number of days which have passed since the contact lenses were last cleaned. This is particularly important inasmuch as a build-up of proteinaceous material on the contact lenses could effect the corrective function of the lenses. Therefore, there further exists a need for a contact lens disinfector unit which includes an indicator to assist the user in determining the number of sterilization cycles which have been employed since the user last cleaned the contact lenses with respect to said proteinaceous material.

It is therefore a general object of the present invention to provide a new and improved contact lens disinfector unit with cycle indicating means to assist the user thereof.

It is a further object of the invention to provide a contact lens disinfector unit which not only indicates that the sterilization temperature has been reached, but additionally includes an indication that the lens case containing the contact lenses and the disinfector unit have sufficiently cooled to facilitate removal of the case from the unit.

It is a further more specific object of the present invention to provide a contact lens disinfector unit which provides the user with the above indications as well as an indication of the number of sterilization cycles which have been employed since the contact lenses were last cleaned, and a further indication when it is again time to clean the contact lenses.

The invention therefore provides a contact lens disinfector unit for sterilizing contact lenses, wherein said lenses are of the type which preferably should be sterilized once each day and periodically cleaned after a predetermined number of days. The disinfector unit comprises a housing including a heating arrangement and circuit means adapted to heat the contact lenses to a sterilization temperature and for terminating the application of heat thereafter to allow the contact lenses to cool for completing a sterilization cycle. The contact lens disinfector unit further includes a sterilization cycle indicating means responsive to temperature changes for providing a first indication responsive to the heating arrangement reaching the sterilization temperature and a second indication responsive to the heating arrangement returning to a reduced temperature or cooled state, and also an indication of the number of sterilizing cycles effected since the last incident of cleaning of the lenses.

BRIEF DESCRIPTION OF THE DRAWINGS

The invention, together with the further advantages thereof, may best be understood by making reference to the following description taken in conjunction with the accompanying drawings, wherein the several figures of which like reference numerals identify like elements, and wherein.

DESCRIPTION OF THE PREFERRED EMBODIMENT

Figure 1:
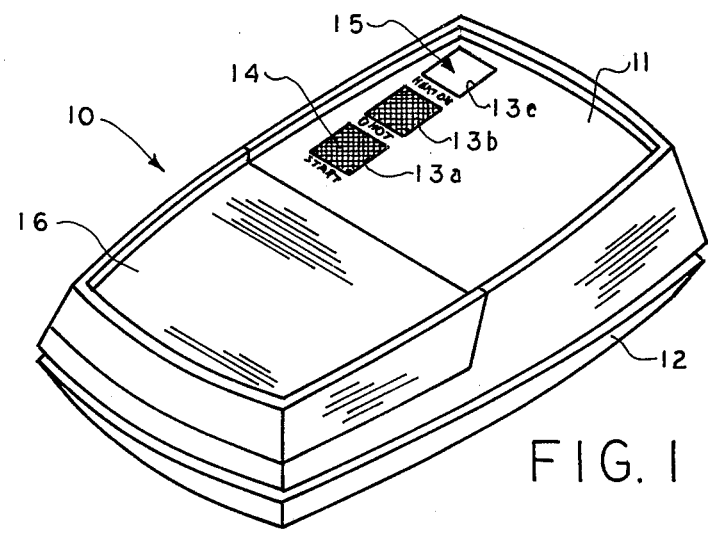
FIG. 1 is a perspective view of a contact lens disinfector unit embodying the present invention.

Referring now to FIG. 1, the disinfector unit 10 there shown includes a housing comprised of a top cover section 11, a bottom section 12, with a plurality of openings 13a, b and c provided in said cover section 11. In a first opening 13a there is provided an activator button 14 mechanically coupled to a thermocouple switch, which button 14, when depressed, initiates a sterilization cycle. The second opening 13b is disposed in relation to an internal light bulb which lights up when the thermocouple switch is closed for indicating that the unit 10 is in the heating mode, with the light bulb beneath the window 13b being deenergized when the thermocouple switch opens upon reaching a sterilization temperature. The opening 13c is disposed above the sterilization cycle indicating means of the present invention and provides a viewing window 15 through which the user may view said indicating means and thus be informed that the contact lenses are heated to the sterilization temperature and, thereafter, that the contact lenses have cooled sufficiently so as to be removed from the disinfector unit, or that cleaning is required.

Figure 2:
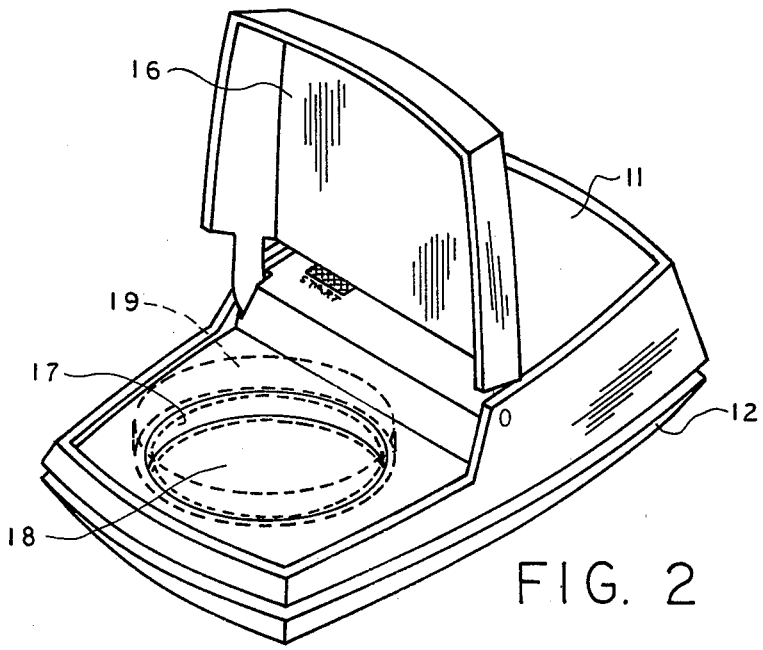
FIG. 2 is a perspective view of the disinfector unit of FIG. 1 showing its hinged cover in a raised position and a contact lens case (shown in dotted lines) in operative position with respect to the heating arrangement contained within the unit.

The top cover section 11 includes a hinged lid portion 16 which is shown in a raised position in FIG. 2. In addition, the top cover 11 includes a circular recess 17 which communicates with the upper surface of a heating block 18 disposed internally of the unit 10, and which recess 17 is dimensioned for receiving a lens case shown in dotted outline, and indicated at 19. The lens case 19 may be of any of several types well-known in the art, which include a bottom portion removably engaged with an upper portion, with one of said portions adapted to accommodate a pair of lenses and a quantity of disinfecting solution. Preferably, the lens case 19 and the recess 17 are dimensioned such that the bottom surface of the lens case makes direct surface-to-surface contact with the upper surface of the heating block 18. As mentioned above, the lens case also includes means for receiving a pair of contact lenses and a quantity of disinfecting or sterilizing solution, which is introduced into the lens case prior to the sterilization of the lenses. During the disinfecting cycle, the heating block 18 provides sufficient heat transfer to the lens case 19 so as to heat the contact lenses and the solution to a sterilization or disinfecting temperature sufficient to kill bacteria on the lenses.

Figure 3:
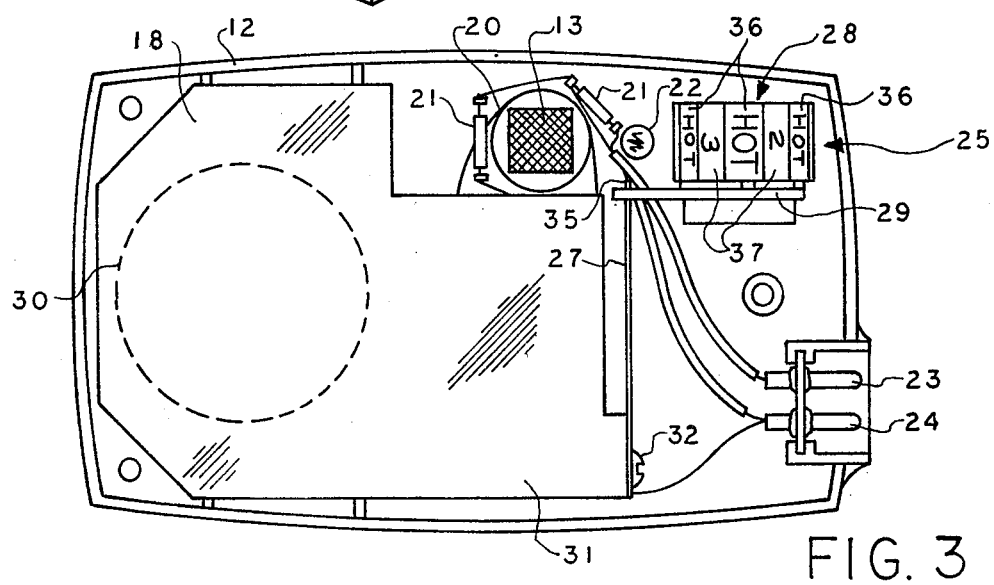
FIG. 3 is a top plan view of the interior of the disinfector unit of FIG. 1, the top or cover portion of the unit housing having been removed.

Referring now to FIG. 3, the disinfector unit 10 is there shown with its top cover section 11 removed, and there is visable a preferred arrangement utilizing the cycle indicating means of the present invention. Basically, the disinfector unit 10 includes the aforementioned heating block 18, a thermocouple switch 20 with its reset button 14 that extends through the opening 13a, a power supply circuit for a resistive heating element, (not shown), including elements designated generally 21, are shown for illustrative purposes, which circuit is adapted to be connected to an electric power source by pins 23 and 24. In addition a light bulb 22 whose function was described previously is provided to underlie opening 13b, and adjacent thereto the sterilization cycle indicating arrangement of the present invention which is designated generally 25, and will be discussed in greater detail hereinafter.

The heating block 18 includes a surface portion 30 shown in dashed lines which engages the undersurface of the lens case during the sterilization of the contact lenses. The heating block includes a rearward portion 31 to which the cycle indicating arrangement 25 is operatively connected. The heating block 18 is in contact with the resistive heating element mentioned above, and due to the surface-to-surface contact with the case 19 applies heat evenly thereto for a sufficient period of time during the sterilization cycle so as to raise the temperature of the sterilizing solution to that required for disinfecting of the contact lenses. The circuit means providing power to the resistive heater is of a type well-known in the art and need not be described in detail herein.

Attention is now directed to the cycle indicating arrangement 25, which is shown in greater detail in FIGS. 4-11. In this regard, said arrangement includes a first, temperature sensative member 27 in the form of a bi-mettalic strip which has one end 32 affixed to the extension 31 and the other end 35 free to move laterally. In this regard, the end 35 will move in a first direction to the right as the temperature of heating block 18 rises and laterally in a second direction to the left as the heating block cools. As will be described more fully hereinafter, the reciprocal lateral movement of the bi-metallic strip 27 is used to impart movement to a second, indicia carrying member 28 which in the illustrated embodiment is in the form of a drum or cylinder. The drum 28 has on its peripheral surface a plurality of indicia including a first set of indicia 36 for indicating that the sterilization temperature has been reached, and a second set of indicia 37 in the form of numbers which correspond to a count of the cycles and also serve to indicate that the heating block and contact lenses have cooled to a reduced temperature to afford the safe removal of the contact lenses from the unit, as will become clearer hereafter. The arrangement 25 further includes third member 29 in the form of a pawl, which member 29 serves to couple the free end 35 of the bi-metallic strip 27 to the drum 28 for imparting the movement to said drum in response to the lateral movement of the bi-metallic strip 27.

Figure 4:
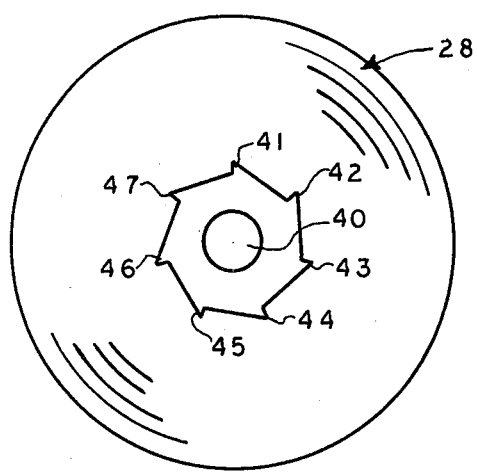
FIG. 4 is a side plan view of one element of the sterilization cycle indicating means of the disinfector unit embodying the present invention.
Figure 5:
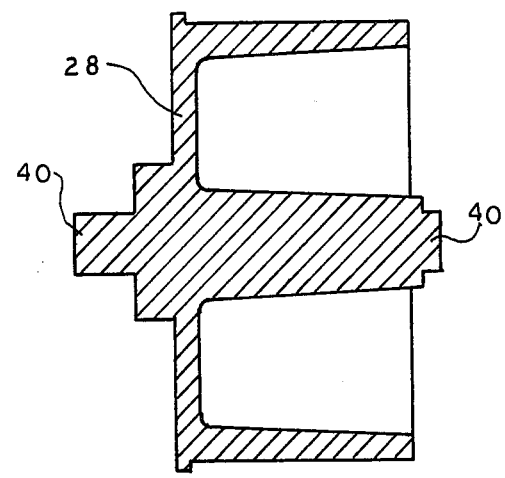
FIG. 5 is a cross-sectional view taken along lines 5—5 of FIG. 4.
Figure 8:
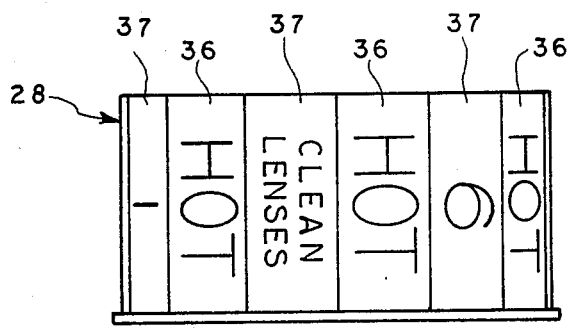
FIG. 8 is a top plan view of the element of FIGS. 4 and 5 with certain indicia means on said element.

More specifically, the drum 28, as may be seen in detail in FIGS. 4, 5 and 8, includes a central mounting shaft 40 which permits said drum to be mounted for rotational movement. Disposed around the shaft in radial position are a plurality of ratchet teeth 41 through 47. In the illustrated embodiment there are seven such ratchet teeth disposed about the shaft 40. As best seen in FIG. 8, the first set of indicia 36 comprise the word "hot" which may be seen through the window 15 of the disinfector unit top cover 11 for indicating that the unit has reached an elevated temperature during the sterilization cycle. The second set of indicia 37 include the consecutive numbers 1-6, and alternate with the first indicia 36, the last indicia of said second set 37 includes the words "clean lenses" to notify the user that seven sterilization cycles have been employed since the contact lenses were last cleaned, and that it is now time to clean the contact lenses.

Figure 6:
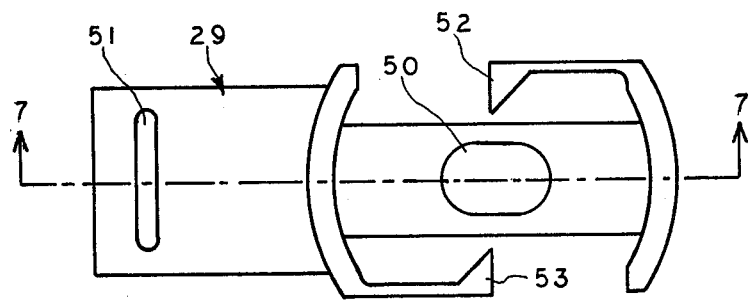
FIG. 6 is a side plan view of another element of the sterilization cycle indicating means of the present invention.
Figure 7:
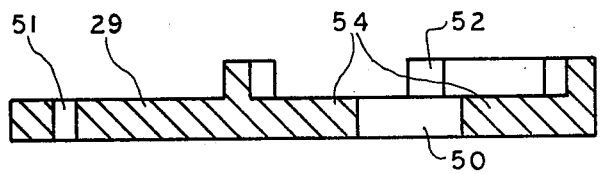
FIG. 7 is a cross-sectional view taken along lines 7—7 of FIG. 6.
Figure 9:
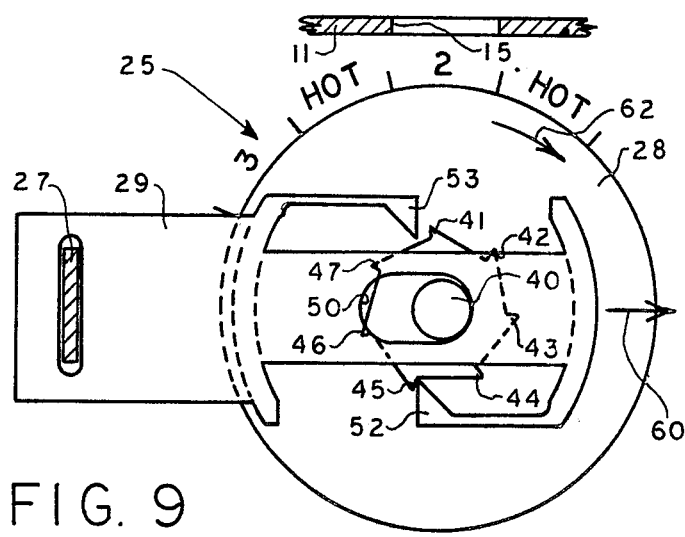
FIGS. 9-11 are side plan views of the elements of FIGS. 4 and 6 in the assembled relation and illustrating the relative movement of these elements and correspondingly the operation of the cycle indicating means of the present invention.
Figure 10:
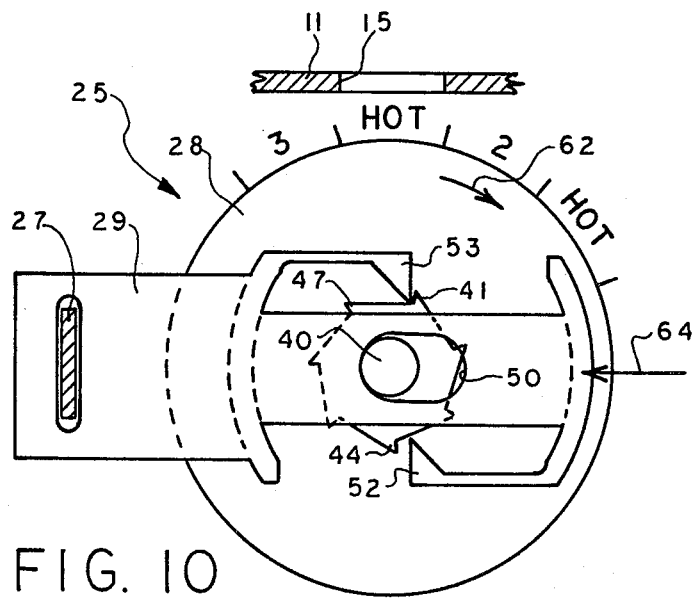
Figure 11:
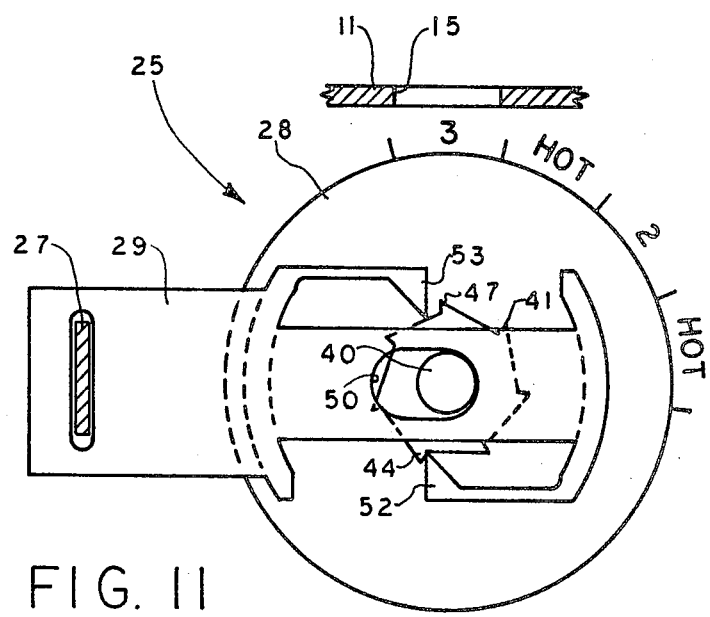

The pawl member 29 is shown in detail in FIGS. 6 and 7, and includes a first slot 50, a second elongated slot 51, and a pair of oppositely disposed, separate pawl elements 52 and 53. The slot 51 is dimensioned for receiving the end 35 of the bi-metallic strip 27 so that the bi-metallic strip 27 is operatively coupled to the pawl member 29. The slot 50 is dimensioned so that the shaft 40 of the drum 28 may be slidably engaged therein so that the pawl 29 can be engaged with the drum 28 for limited relative movement as shown in FIGS. 9-11, and for a purpose to be detailed. As can be seen from FIGS. 6 and 7, the pawl element 52 and 53 are laterally offset from the surface 54 of the pawl member surrounding the inner portion of slot 50, so that the pawl elements 52 and 53 will be in operative alignment with the ratchet teeth 41 through 47 when the pawl 29 is mounted to the drum 28. The slot 50 is elongated to allow for limited reciprocating movement of the pawl 29 during operation of the disinfector unit.

FIGS. 9-11 illustrate how the pawl member 29 is mounted to the drum 28 in cooperative relation, and further illustrates the operation of the sterilization cycle indicating means of the present invention. More specifically, FIG. 9 illustrates the condition of the indicating means prior to the start of a sterilization cycle. For purposes of illustration and discussion, the drum 28 is shown with the number "2" of the second set of indicia 37 at the top of the drum surface 28 and in register with the viewing window 15 of the disinfector unit top cover 11. After the sterilization cycle has been initiated for sufficient period of time the temperature of the heating block 18 rises causing the bi-metallic strip 27 to flex in a first direction, i.e., to the right as viewed. This flexing of the bi-metallic strip 27 will cause the free end 35 and correspondingly pawl member 29 to move laterally in the first direction towards the right as indicated by arrow 60. The drum 28 is free to rotate, being fixed against lateral movement, such that the pawl member 29 will move relative to said drum 28, with the slot 50 defining the limits of movement. Accordingly, this relative movement will cause the upper pawl element 53, as viewed, to engage the ratchet tooth 41 to effect an increment of rotative movement of the drum 28 in the clockwise direction, as indicated by arrow 62. As the drum 28 rotates the lower pawl element 52 will ratchet with respect to the ratchet tooth 44. This increment of movement is essentially equal to 1/14 of a complete revolution, and will cause the "hot" indicia between the numbers "2" and "3" to appear at the top surface of the drum 28, beneath the viewing window 15. After the increment of movement described has taken place, the indicating means 25 will be generally in a condition as illustrated in FIG. 10. In this regard, it should be noted that the hub 40 engaged in slot 50 precludes further movement in the direction 60, and that the lower pawl element 52 has ratcheted past the tooth 44.

As the heating block and lens case cool subsequent to completion of the sterilization procedure, the bi-metallic strip 27 and correspondingly, pawl member 29 will move laterally in the second direction towards the left as indicated by arrow 64, FIG. 10. This movement of the pawl member 29 serves to cause the lower pawl element 52 to engage the ratchet tooth 44 to effect an additional increment of movement in the clockwise direction 62. As the drum 28 rotates, the pawl element 53 will ratchet with respect to the ratchet tooth 47, with the relation of the slot 50 and hub 40 limiting the movement of the pawl member 29 and correspondingly the rotation of drum 28. Thus, as the bi-metallic strip 27 returns to its initial position upon cooling, the drum 28 will be caused to rotate an additional 1/14 of a complete revolution to the condition as shown in FIG. 11.

Looking to FIG. 11, as a result of the movement of the drum through a second rotational increment, the indicia bearing "3" appears at the top of the drum 28 and will be visable through the window 15. The appearance of the number "3" provides two indications to the user, first, that the sterilization cycle has been completed and that the lens case and contact lenses have cooled sufficiently for removal and use without risk of injury, and secondly, it provides a count as to the number of cycles employed.

As is further shown in FIG. 11 the cycle counter or indicator arrangement 25 has been reset, such that the next sterilization cycle will produce similar incremental movement of the drum 28, with the ratchet means provided by the pawl elements 52, 53 and ratchet teeth 41-47 limiting said movement to the clockwise direction 62. Thus, the drum 28 will continue to be rotated as the unit 10 is used, and upon completion of the seventh cycle, the indicia "Clean Lenses", as shown in FIG. 8 will appear in the window 15, to remind the users to effect removal of the proteinaceous material which may have formed on the lenses.

From the foregoing, it can be appreciated that the present invention provides an improved contact lens disinfector unit with a sterilization cycle indicating means that not only provides an indication that the contact lenses have been heated to the sterilization temperature, but further, provides a second indication indicating that the contact lenses have sufficiently cooled. Furthermore, with the use of a second set of indicia 37 employing six consecutively numbered indicia and a seventh indicia to remind the user that it is time to clean the contact lenses, the present invention additionally indicates to the user that it is now time to clean the lenses once again.

While a particular embodiment of the present invention has been shown and described, modifications may be made, and it is therefore intended to cover in the appended claims all such changes and modifications which fall within the spirit and scope of the invention, as defined by said claims.

The invention is claimed as follows:

1. A contact lens disinfector unit for sterilizing contact lenses contained within a contact lens case, wherein the contact lenses are of the type which preferably should be cleaned periodically after a predetermined number of sterilizing cycles, said disinfector unit comprising: a heating block arranged to contact the contact lens case; circuit means coupled to said heating block and adapted to be coupled to a source of electric potential for applying electric current to said heating block for a sufficient time period for causing said heating block to heat the lens case and the contact lenses contained therein to a sterilizing temperature and for terminating the application of said electric current to said heating block thereafter to allow the lens case and the contact lenses to cool for completing a contact lens sterilizing cycle; and sterilizing cycle indicating means including indicia bearing indexing means responsive to the temperature changes of said heating block for providing a first indication responsive to said heating block reaching said sterilizing temperature and a second indication responsive to said heating block returning to a reduced temperature below said sterilizing temperature, thereby providing a positive indication that the sterilizing cycle has taken place and is completed.

2. A contact lens disinfector unit as defined in claim 1, wherein said indicia bearing indexing means includes a first set of spaced indicia to indicate that the sterilizing temperature has been reached, and a second set of indicia alternating with said first set of indicia for providing said second indication, as well as the number of sterilizing cycles completed from a given datum point.

3. A disinfector unit as defined in claim 1 wherein said indicia bearing indexing means comprises a first member arranged to move laterally in response to said heating block temperature changes and a second member rotatable by said first member, said second member including sterilizing cycle indicia for providing said first and second indications, and ratchet means interconnecting said first member and said second member, such that movement of said first member will produce rotation of said second member in but one direction.

4. A disinfector unit as defined in claim 3 wherein said indicia comprises a first plurality of indicia for indicating when said heating block reaches said sterilizing temperature and a second plurality of indicia alternating with said first plurality of indicia for providing said second indication and the number of sterilizing cycles which have been completed since the contact lenses were last cleaned and wherein the last indicia of said second plurality provides an indication that the contact lenses should be cleaned.

5. A disinfector unit as defined in claim 3 wherein said first member comprises a bi-metallic strip mounted to said heating block and arranged to move laterally at one end thereof in a first direction responsive to the heating of said block, and in a second direction responsive to the cooling of said block.

6. A disinfector as defined in claim 5 wherein said second member comprises a cylindrical drum having a shaft and wherein said drum includes said indicia about its periphery.

7. A disinfector as defined in claim 6 wherein said ratchet means comprises a pawl member engaged and movable with said first member, and wherein said drum includes a plurality of ratchet teeth equally spaced about said shaft, said pawl member being coupled to one end of said bimetallic strip and arranged to engage said ratchet teeth as said end of said bimetallic strip moves laterally for rotating said drum.

8. A disinfector as defined in claim 7 wherein said pawl member includes a pair of pawls for rotating said drums responsive to movement of said bimetallic strip in said first direction and for rotating said drum responsive to movement of said bimetallic strip in said second direction.

9. A disinfector as defined in claim 8 wherein said pawl member includes a first elongated slot at one end thereof dimensioned to receive said drum shaft for mounting said pawl member onto said drum.

10. A disinfector as defined in claim 9 wherein said pawl member includes a second elongated slot at the other end thereof for receiving and being coupled to said one end of said bimetallic strip.

11. A contact lens disinfector unit for sterilizing contact lenses contained within a contact lens case, said disinfector unit comprising: a heating block arranged to contact the contact lens case; circuit means coupled to said heating block and adapted to be coupled to a source of electric potential for applying electric current to said heating block for a sufficient time period for causing said heating block to heat the lens case and the contact lenses contained therein to a sterilization temperature and for terminating the application of said electric current to said heating block thereafter to allow the lens case and the contact lenses to cool for completing a contact lens sterilization cycle; and sterilization cycle indicating means comprising, a viewing window, a first member laterally moveable in first and second directions responsive to the temperature changes of said heating block, a second member mounted for rotational movement beneath said viewing window, said second member bearing a first set of indicia visable through said window when aligned therewith, and indicating that the sterilization temperature has been reached, and a second plurality of indicia, alternating with said first plurality, also alignable with said viewing window for indicating that the sterilization cycle has been completed, and ratchet means including a third member coupling said first member to said second member for imparting rotational movement to said second member in but one direction responsive to the lateral movement of the first member for causing one of said first and second indicia to occur beneath said viewing window during each sterilization cycle.

12. A contact lens disinfector unit for sterilizing contact lenses, said disinfector unit comprising: a housing with heating means contained therein and to effect heating of the contact lenses to a sterilization temperature and for terminating the application of heat thereafter to allow the contact lenses to cool for completing a contact lens sterilization cycle; and sterilization cycle indicating means comprising, a viewing window formed in said housing, a first bimetallic member laterally moveable in first and second directions responsive to the temperature changes of said heating means, a second member mounted for movement beneath said viewing window, said second member bearing indicia means visable through said window when aligned therewith and indicating that the sterilization temperature has been reached, and for indicating that the sterilization cycle has been completed, and ratchet means including a third member coupling said first bimetallic member to said second member for imparting rotational movement to said second member in but one direction in response to the lateral movement of the first member for causing one of said indicia to occur beneath said viewing window during each sterilization cycle.

13. A disinfector unit according to claim 12 wherein said indicia means include a first set of indicia indicating that the desired sterilizing temperature has been reached, and a second set of indicia alternating with said first set indicating completion of the sterilization cycle, with movement of said first bimetallic member in said first direction bringing one of said first indicia in alignment with said viewing window, and movement to said second direction advancing said second member to bring one of said second set of indicia into alignment with said window.

14. A disinfector unit according to claim 12 wherein said second member comprises a drum mounted for rotational movement, with said indicia means carried on the periphery thereof.

15. A disinfector unit according to claim 14 wherein said ratchet means includes a plurality of ratchet teeth on said drum, and said third member includes a pair of oppositely facing pawl elements engagable with said drum ratchet teeth, such that reciprocal movement of said third member will be converted into rotational movement of said drum.

16. A cycle indicating arrangement for a heating device such as a contact lens sterilizer, or the like, which arrangement provides an indication as to attainment of completed heating cycle, said arrangement including, an elongate bimetallic member disposed in close proximity to an element of the heating device so as to be responsive to the heat generated, one end of said bimetallic member being fixed with the other end free to move as the member flexes in response to temperature change, an indicia bearing member mounted for relative movement so as to sequentially move the indicia thereon with respect to viewing means provided by said device, and ratchet means for effecting movement of said indicia bearing member in response to flexing of said bimetallic member, said ratchet means including a pawl member operatively associated with said elongate bimetallic member to move in a reciprocating manner in response to the flexing of said bimetallic member, and interengaged means on said pawl member and on said indicia bearing member, such that the flexing of said bimetallic member in response to a heating cycle will produce reciprocal movement of said pawl member, which in turn effects movement of said indicia bearing member.

17. An arrangement according to claim 16, wherein said indicia bearing member is a drum rotatably mounted, with indicia on the periphery thereof, and said ratchet means includes a plurality of ratchet teeth thereon and disposed radially to limit rotation of the drum to a single direction.

18. An arrangement according to claim 16 wherein the indicia on said indicia bearing member includes a first set of spaced indicia indicating attainment of a desired temperature, and a second set of indicia alternating with said first set, and indicating the cycle completion, and said ratchet means including means for effecting incremental movement of said indicia bearing member in but a single direction in response to the flexing of said bimetallic member, such that when said bimetallic member flexes in response to an elevated temperature, one of said first set of indicia will be viewable through said viewing means, with movement of the bimetallic member in response to cooling advancing said indicia bearing member such that one of said second set of indicia will be viewable, with the limitation of movement to a single direction bringing said second indicia into view sequentially.

19. An arrangement according to claim 18 wherein said indicia bearing member is a rotatably mounted drum with said first and second set of indicia on the periphery thereof, and said ratchet means including, a plurality of ratchet teeth on said drum and disposed radially to limit drum movement to a single direction, and first and second oppositely disposed pawl elements on said reciprocating pawl member, such that when said pawl member moves in a first direction said first pawl elements will engage said ratchet teeth to effect an incrememt of movement while the said second pawl element ratchets, and when said pawl member moves in a second, opposite direction said second pawl element engages said ratchet teeth, while said first pawl element ratchets, whereby for each heating cycle at least two increments of movement of said drum will be effected.

* * * * *